United States Patent [19]

Peyman

[11] 4,099,529
[45] Jul. 11, 1978

[54] WIDE-ANGLE CUTTER VITROPHAGE

[76] Inventor: Gholam A. Peyman, 1044 N. Oak Park Ave., Oak Park, Ill. 60302

[21] Appl. No.: 724,709

[22] Filed: Sep. 20, 1976

[51] Int. Cl.² ............................................. A61B 17/32
[52] U.S. Cl. ..................................... 128/305; 30/247; 128/276
[58] Field of Search ............... 128/276, 305, 277, 2 B; 30/180, 228, 241, 229

[56] References Cited

U.S. PATENT DOCUMENTS

| | | | |
|---|---|---|---|
| 3,776,238 | 12/1973 | Peyman et al. | 128/305 |
| 3,815,604 | 6/1974 | O'Malley et al. | 128/305 |
| 3,884,238 | 5/1975 | O'Malley et al. | 128/305 |
| 3,902,498 | 9/1975 | Niederer | 128/305 |
| 3,995,619 | 12/1976 | Glatzer | 128/2 B |

Primary Examiner—Robert W. Michell
Assistant Examiner—Michael H. Thaler

[57] ABSTRACT

An improved vitrectomy instrument having a small diameter cutting probe comprising coaxial inner and outer tubes. The outer tube is formed with a triangular cutting aperture with the base of the triangle forming a step or ledge adjacent to the tip of the probe and transverse to the axis of the tube. The sides of the triangular aperture are tapered in cylindrical section along the side of the outer tube. The inner tube is adapted to oscillate longitudinally within the outer tube and the end of the inner tube forms a shearing edge with the base of the aperture. The base or ledge functions as a hook to catch the edges of semi-solid membranes to be severed.

1 Claim, 5 Drawing Figures

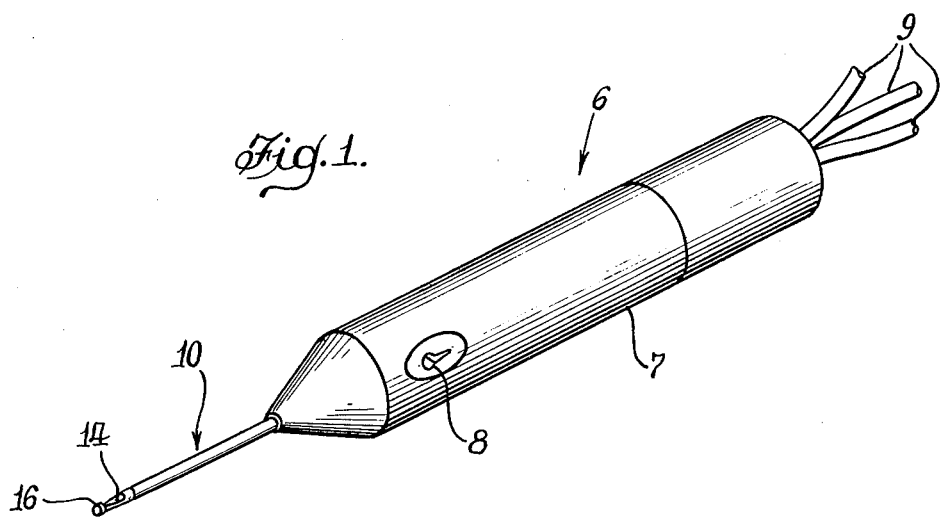
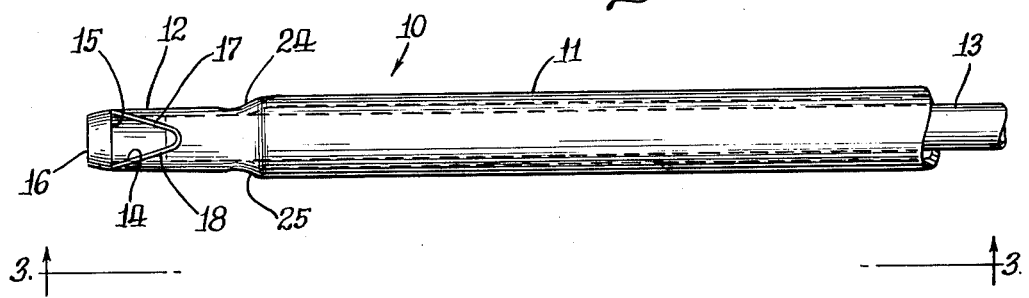
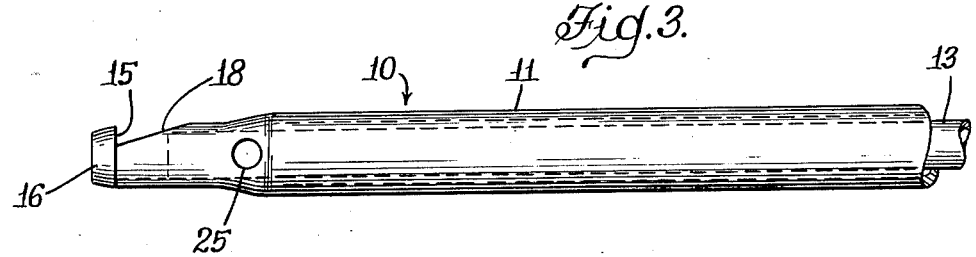
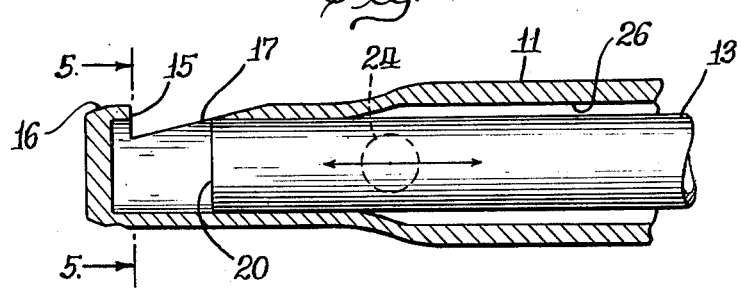
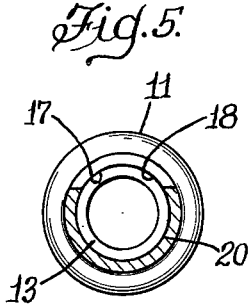

WIDE-ANGLE CUTTER VITROPHAGE

BACKGROUND OF THE INVENTION

1. Field of the Invention

This invention relates generally to the field of Surgery, and more particularly to instruments and cutters for performing intraocular surgery.

2. Description of the Prior Art

Beginning in the late 1950s and early 1960s, a number of modern methods for performing vitreous surgery were developed. These new methods included the development of a number of automated instruments to remove and replace vitreous.

Several of the instruments developed for these tasks have been illustrated and described by Hennig, J. & Bormann, H. in: Geräte zur Vitrektomie. Klin Monatsbl Augenheilkd 166:29, 1975; and by Peyman, G. A. & Sanders, D. R. in: Advances in Uveal Surgery, Vitreous Surgery, and the Treatment of Endophthalmitis. Appleton-Century-Crofts, 1975. All of these devices included a small tube or probe formed with an aperture near the tip and adapted to be inserted into the eye, an internal cutting tube or rotating burr, and some form of suction means for withdrawing severed tissue. The instruments employing rotating curring bits frequently wound up the fibrous tissue to be removed and tore the tissue rather than severed it. Nearly all of the present suction cutters operate in such a way that tissue must be drawn into an opening before it is severed by the cutting mechanism. Especially taut membranes resist this movement, however, and are difficult to manage.

In my earlier U.S. Pat. No. 3,776,238, entitled: OPHTHALMIC INSTRUMENT, there was described an instrument consisting of two tubes mounted coaxially within one another, and with an opening adjacent to the end of the outer tube. Cutting of the vitreous and fibrous bands was performed by a chopping action set up by the sharp end of the inner tube against the inner surface of the end of the outer tube.

The instrument described in this patent was found to have some limitations in use. For one, the chopping action tended to dull the cutting edge on the inner tube so that it would not cut cleanly thereafter. The failure to cut cleanly inhibited the removal by suction of the tissue severed.

The U.S. Pats. to O'Malley, Nos. 3,884,237 & 3,884,238, also describe APPARATUS FOR INTRAOCULAR SURGERY having a probe consisting of concentric tubes of small diameter. The inner tube is moved longitudinally within the outer tube to provide a cutting action at the edges of an aperture formed through the wall of the outer tube. Vitreous material to be severed is sucked into the aperture and sheared off by the cutting edge of the end of the inner tube. The aperture per se is generally triangular in configuration with the tapered sides and a base transverse to the axis of the tube. The orientation of the base is such that the cutting edge of the inner tube forces the vitreous material away, rather than shearing against the edge of the base.

SUMMARY OF THE INVENTION

It is the object of the present invention to provide an improved vitrectomy instrument having a probe formed with a wide-angle cutting aperture effective to engage fibrous tissue in the manner of a crochet hook and an internal oscillating tube effective to sever such tissue by a guillotine cutting action.

BRIEF DESCRIPTION OF THE DRAWINGS

FIG. 1 is a perspective elevation view of the wide-angle cutter instrument of the present invention;

FIG. 2 is an enlarged fragmentary elevation view, partially in phantom, of the cutter probe of FIG. 1;

FIG. 3 is an elevation side view taken on line 3—3 of FIG. 2;

FIG. 4 is an enlarged fragmentary section view of the cutting aperture and probe tip; and FIG. 5 is a sectional end view taken on line 5—5 of FIG. 4.

DESCRIPTION OF THE PREFERRED EMBODIMENT

The wide-angle cutter vitrectomy instrument of the present invention is illustrated in FIG. 1 and is designated generally by the numeral 6. The instrument 6 comprises a cylindrical handle or housing 7 formed with a suction control port 8, a plurality of fluid and suction conduits 9, and an elongate small-diameter cutting probe 10. The probe 10 comprises an external tubular housing 11 formed with a cutting tip 12 of reduced diameter, and an internal cutting tube 13. The tip 12 is formed with a generally triangular, or wide-angle notch or aperture 14 cut through its cylindrical wall. The base 15 of the triangular aperture 14 is adjacent to the rounded end 16 of the tip 12 and is transverse to the axis of the tube 11. The sides 17 and 18 of the aperture 14 follow the contour of the cylindrical wall of the tip 12. All of the edges 15, 17, and 18 are honed to razor sharpness and form shearing edges with the lower end 20 of the internal tube 13.

The tube 13 is disposed to oscillate longitudinally within the tube 11 and its oscillatory motion carries the end 20 past the aperture 14. The end 20 is also honed to razor sharpness and makes shearing contact principally against the edge 15 at the base of the aperture 14. The mechanism (not shown) for causing the oscillatory motion of the tube 13 is connected to a source of suction and contained within the handle 7. The upper end of the tube 13 is also connected to a suction source (not shown) which is effective to remove severed tissue through the tube 13.

The tube 11 is also formed with one or more infusion apertures 24 and 25 immediately above the tip 12. As tissue and fluid are removed from the eye, replacement fluid is introduced through the apertures 24 and 25. The replacement fluid is supplied from a source (not shown) through the space 26 between the tubes 11 and 13. The replacement fluid may be infused in the manner described in my earlier U.S. Pat. No. 3,776,238.

In operation, the instrument 6 functions as follows: The probe 10 is inserted into the eye of the patient and the ledge 15 engages or hooks tissue to be removed. The longitudinal cutting motion of the internal tube 13 is controlled by the surgeon by placing and removing a finger over the control port 8. The shearing edge 20 of the tube 13 moves past the aperture 14 and severs the tissue engaged by the ledge 15 in a guillotine cutting action. The tissue severed by the edge 20 is removed by suction through the tube 13. Replacement fluid is infused through the ports 24 and 25 as required. The operation described is repeated as required to nibble away all of the tissue to be removed.

It should be noted that the operation of this instrument differs substantially from the prior art devices that required the tissue to be removed to be sucked into the aperture before it could be severed. In the instrument of the present invention, the tissue to be removed, which is often fibrous in nature, is physically engaged or hooked by the base of the aperture before being severed. It has been found by practical experience to be significantly superior to all known devices of this type.

It is to be understood that many changes and modifications may be made without departing from the spirit of the present invention. The embodiment shown and described is not to be considered as limited thereto, except insofar as the claims may be so limited.

I claim:

1. A surgical instrument for performing intraocular surgery involving the removal of fibrous tissue from within the eye of a patient and having a control handle carrying a small diameter probe for insertion into the eye comprising:

an external tube as part of the probe having an external wall and a longitudinal axis and formed with a closed end tip and a generally triangular shaped aperture in its external wall;

said triangular aperture being oriented with a base edge tranverse to said longitudinal axis in close proximity to and adjacent said tip and defining a tissue engaging ledge and with an apex of said aperture being remote from said tip said base edge lying in a plane perpendicular to said longitudinal axis;

an internal cutting tube coaxial with and telescoped within said external tube having a driven end and a free end with a sharp cutting edge formed on said free end;

drive means connected to said driven end for causing controlled longitudinal oscillation of said internal tube within said external tube and operable in its oscillation to carry said cutting edge past said base edge of said aperture; and means defining a sharp shearing edge formed on an inner edge of said aperture base and effective in shearing coaction with said cutting edge of said internal tube to cleanly sever tissue engaged by said ledge.

* * * * *